US009486613B2

(12) United States Patent
Dickert et al.

(10) Patent No.: US 9,486,613 B2
(45) Date of Patent: Nov. 8, 2016

(54) CATHETER SECUREMENT DEVICE WITH SLIT BETWEEN FIRST AND SECOND PULL TABS

(75) Inventors: Aaron M. Dickert, Lansing, MI (US); Tamer Elsamahy, Brighton, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 685 days.

(21) Appl. No.: 12/914,220

(22) Filed: Oct. 28, 2010

(65) Prior Publication Data
US 2012/0109069 A1    May 3, 2012

(51) Int. Cl.
*A61M 25/02* (2006.01)
*A61M 5/158* (2006.01)

(52) U.S. Cl.
CPC ...... *A61M 25/02* (2013.01); *A61M 2005/1586* (2013.01); *A61M 2025/024* (2013.01); *A61M 2025/0246* (2013.01); *A61M 2025/0266* (2013.01)

(58) Field of Classification Search
CPC ............... A61M 2025/0273; A61M 25/02; A61M 5/32; A61M 5/158
USPC ............... 604/174–180, 533, 164.04, 891.1; 128/847, 888, 200.26
See application file for complete search history.

(56) References Cited

U.S. PATENT DOCUMENTS

| 3,167,072 A | * | 1/1965 | Stone | A61M 25/02 128/DIG. 26 |
| 3,677,250 A | * | 7/1972 | Thomas | A61M 25/02 128/DIG. 26 |
| 3,834,380 A | * | 9/1974 | Boyd | A61M 25/02 128/DIG. 26 |
| 3,900,026 A | * | 8/1975 | Wagner | A61M 25/02 128/888 |
| 4,057,066 A | * | 11/1977 | Taylor | A61M 25/02 128/DIG. 26 |
| 4,133,307 A | * | 1/1979 | Ness | A61M 25/02 602/32 |
| 4,224,937 A | * | 9/1980 | Gordon | A61M 25/02 128/DIG. 26 |
| 4,250,880 A | * | 2/1981 | Gordon | A61M 25/02 128/DIG. 26 |
| 4,324,236 A | * | 4/1982 | Gordon | A61M 25/0637 128/DIG. 26 |

(Continued)

*Primary Examiner* — Bhisma Mehta
*Assistant Examiner* — Matthew A Engel
(74) *Attorney, Agent, or Firm* — Kristin L. Murphy; Brooks Kushman P.C.

(57) ABSTRACT

A catheter securement device in accordance with the present invention includes a flexible base member having an adhesive side and an opposite non-adhesive side. A single piece elastomeric anchoring member is mounted on the non-adhesive side of the base member. The anchoring member integrally includes a pair of opposing pull tabs, a slit disposed between the opposing pull tabs, and a third pull tab disposed between the slit and one of the opposing pull tabs. Pulling the opposing pull tabs opens the slit for receiving a catheter hub in the slit, and the third pull tab is insertable into the slit for securing the catheter hub between the anchoring member and the base member.

23 Claims, 4 Drawing Sheets

(56) References Cited

U.S. PATENT DOCUMENTS

| | | | | |
|---|---|---|---|---|
| 4,392,856 | A * | 7/1983 | Lichtenstein | A61M 25/0637 604/177 |
| 4,392,857 | A * | 7/1983 | Beran | A61M 25/02 128/207.17 |
| 4,571,245 | A * | 2/1986 | Hubbard | A61M 25/02 128/DIG. 26 |
| 4,617,017 | A * | 10/1986 | Hubbard | A61M 25/02 128/DIG. 26 |
| 4,702,736 | A * | 10/1987 | Kalt | A61M 25/02 128/DIG. 26 |
| 4,820,282 | A * | 4/1989 | Hogan | A61M 25/0637 128/DIG. 26 |
| 4,838,867 | A * | 6/1989 | Kalt | A61M 25/02 128/DIG. 26 |
| 4,838,878 | A * | 6/1989 | Kalt | A61M 25/02 128/DIG. 26 |
| 5,073,170 | A * | 12/1991 | Schneider | A61M 25/02 128/DIG. 26 |
| 5,085,639 | A * | 2/1992 | Ryan | A61M 5/3243 604/110 |
| 5,147,322 | A * | 9/1992 | Bowen | A61M 25/02 128/DIG. 26 |
| 5,266,401 | A * | 11/1993 | Tollini | A61M 25/02 128/877 |
| 5,300,037 | A * | 4/1994 | Delk | A61M 25/02 128/DIG. 26 |
| 5,322,514 | A * | 6/1994 | Steube | A61M 25/0668 604/177 |
| 5,354,281 | A * | 10/1994 | Chen | A61M 25/0637 604/165.03 |
| 5,380,294 | A * | 1/1995 | Persson | A61M 25/02 604/177 |
| 5,397,639 | A * | 3/1995 | Tollini | A61M 25/02 128/877 |
| 5,501,216 | A * | 3/1996 | Byrd | A61M 25/02 128/200.26 |
| 5,664,581 | A * | 9/1997 | Ashley | A61M 25/02 128/876 |
| 5,681,290 | A * | 10/1997 | Alexander | A61M 25/02 604/174 |
| 5,707,703 | A * | 1/1998 | Rothrum | A61M 25/02 128/849 |
| 5,941,856 | A * | 8/1999 | Kovacs | A61M 25/02 128/DIG. 26 |
| 5,951,522 | A * | 9/1999 | Rosato | A61M 25/0637 604/162 |
| 6,132,398 | A * | 10/2000 | Bierman | A61M 25/02 128/DIG. 26 |
| 6,132,399 | A * | 10/2000 | Shultz | A61M 25/02 604/174 |
| 6,224,571 | B1 * | 5/2001 | Bierman | A61M 25/02 604/174 |
| 6,317,933 | B1 * | 11/2001 | Suenaga | A44B 18/0088 24/16 R |
| 6,413,240 | B1 * | 7/2002 | Bierman | A61M 25/02 128/DIG. 26 |
| 6,419,660 | B1 * | 7/2002 | Russo | A61M 25/02 128/DIG. 26 |
| 6,537,255 | B1 * | 3/2003 | Raines | A61M 5/158 604/177 |
| 6,565,537 | B2 * | 5/2003 | Tollini | A61M 25/02 604/174 |
| 6,743,186 | B2 * | 6/2004 | Crawford | A61M 25/0637 600/583 |
| 6,827,706 | B2 * | 12/2004 | Tollini | A61M 25/02 128/DIG. 26 |
| 6,877,167 | B2 * | 4/2005 | Korkor | A41D 13/1245 2/104 |
| 6,911,020 | B2 * | 6/2005 | Raines | A61M 5/158 604/177 |
| 7,025,749 | B2 * | 4/2006 | Propp | A61M 25/02 604/180 |
| 7,294,118 | B2 * | 11/2007 | Saulenas | A61M 25/0637 604/110 |
| 7,626,070 | B2 * | 12/2009 | Propp | A61M 25/02 602/41 |
| 7,637,894 | B2 * | 12/2009 | Fleischer | A61M 25/02 604/174 |
| D608,444 | S * | 1/2010 | Kyvik | D24/130 |
| 7,753,878 | B2 * | 7/2010 | Jones | A61M 5/158 604/110 |
| 7,793,892 | B1 * | 9/2010 | Bowen | A61M 39/08 128/DIG. 26 |
| 7,824,378 | B2 * | 11/2010 | Jones | A61M 25/0631 604/138 |
| 7,981,087 | B2 * | 7/2011 | Gesler, III | A61M 25/02 128/DIG. 26 |
| 8,052,648 | B2 * | 11/2011 | Dikeman | A61M 25/02 604/174 |
| 8,100,862 | B2 * | 1/2012 | Bierman | A61M 25/02 604/174 |
| 8,162,898 | B1 * | 4/2012 | Wright | A61M 5/158 24/269 |
| 8,211,063 | B2 * | 7/2012 | Bierman | A61M 25/02 604/174 |
| 8,251,957 | B2 * | 8/2012 | Kyvik | A61M 25/02 604/174 |
| 8,540,680 | B2 * | 9/2013 | Burn | A61M 5/158 604/174 |
| 8,636,699 | B2 * | 1/2014 | Russo | A61M 25/02 604/174 |
| 9,248,259 | B2 * | 2/2016 | Kyvik | A61M 25/02 |
| 9,358,366 | B2 * | 6/2016 | Kyvik | A61M 25/02 |
| 2005/0076921 | A1 * | 4/2005 | Rozier | A61M 25/02 128/877 |
| 2005/0215953 | A1 * | 9/2005 | Rossen | A61M 25/02 604/180 |
| 2005/0261623 | A1 * | 11/2005 | Propp | A61M 25/02 604/19 |
| 2006/0041233 | A1 * | 2/2006 | Bowen | A61M 25/02 604/180 |
| 2007/0078400 | A1 * | 4/2007 | Gesler | A61M 25/02 604/177 |
| 2008/0045905 | A1 * | 2/2008 | Chawki | A61F 13/02 604/174 |
| 2008/0097334 | A1 * | 4/2008 | Dikeman | A61M 25/02 604/180 |
| 2009/0143741 | A1 * | 6/2009 | Burn | A61M 5/158 604/177 |
| 2009/0281502 | A1 * | 11/2009 | Heitkamp | A61M 25/02 604/179 |
| 2011/0166529 | A1 * | 7/2011 | LeLievre | A61M 25/02 604/180 |
| 2012/0109070 | A1 * | 5/2012 | Elsamahy | A61M 25/02 604/179 |
| 2012/0226237 | A1 * | 9/2012 | Russo | A61M 25/02 604/177 |

* cited by examiner

CATHETER SECUREMENT DEVICE WITH SLIT BETWEEN FIRST AND SECOND PULL TABS

TECHNICAL FIELD

This invention relates to catheter securement devices, and more particularly to securement devices for securing catheters to a patient's skin.

BACKGROUND OF THE INVENTION

It is known in the art relating to catheters that after insertion of a catheter through a patient's skin into a vein, the catheter must be secured to prevent the catheter from slipping out of the patient's vein. Commonly, surgical tape is used to hold the catheter hub or tubing connected to the catheter to the patient's skin. Oftentimes, this method is ineffective to permanently, securely anchor the catheter and to prevent catheter movement.

Further, inadvertent movement of a catheter while the catheter is inserted in a vein is a leading cause of premature catheter failure. When a catheter moves in a vein, it scrapes and pokes the inner wall of the vein, thereby irritating the vein. Repeated movement of the catheter thereby causes sufficient irritation of the vein to require the catheter to be removed and a new catheter inserted in a different location along the same vein or in an entirely new vein. This is costly as it results in a waste of resources. Also, repeated movement of an inserted catheter can cause migration of the catheter in the vein or worse, may lead to the catheter being removed from the vein. Therefore, a need exists for effective anchoring/securement devices for catheters.

Moreover, catheter insertion sites are often dressed with a dressing to protect the insertion site from infection and the like. As a matter of course, these dressings as well as the catheter anchoring means (e.g., tape) must be periodically removed and replaced. For example, dressings and anchoring means may be routinely changed on a weekly basis. The catheter itself, however, if not disturbed, in certain cases can be reanchored, redressed, and left in the vein for a longer period of time. Removal of expired anchoring means and dressings, however, can undesirably cause disturbance/movement of the catheter to the point that the catheter must be removed and replaced. Therefore, a need exists for an anchoring means that can be removed from the catheter without damaging the catheter.

SUMMARY OF THE INVENTION

The present invention provides a catheter securement device that securely anchors a catheter to a patient's skin while at the same time is easily removed from the catheter without damaging the catheter or disturbing the catheter insertion site. The present catheter securement device is designed to be used to anchor catheters having wings, such as suture wings extending from a hub of the catheter. For example, one intended use of the present catheter securement device is to secure PICCs (Peripherally Inserted Central Catheters), but the catheter securement device may be used to secure any winged-type catheter. The present catheter securement device prevents stresses applied to the catheter hub or luer connectors attached to the catheter from transferring to the catheter insertion site and causing catheter migration or removal as well as insertion site irritation.

More particularly, a catheter securement device in accordance with the present invention includes a flexible base member having an adhesive side and an opposite non-adhesive side. A single piece elastomeric anchoring member is mounted on the non-adhesive side of the base member. The anchoring member integrally includes a pair of opposing pull tabs, a slit disposed between the opposing pull tabs, and a third pull tab disposed between the slit and one of the opposing pull tabs. Pulling the opposing pull tabs opens the slit for receiving a catheter hub in the slit, and the third pull tab is insertable into the slit for securing the catheter hub between the anchoring member and the base member.

The third pull tab may extend at an angle relative to the base member. The angle may be generally in the range of approximately 0 to 180 degrees. The base member and the pair of opposing pull tabs may be generally coplanar, and the third pull tab may be disposed at an angle relative to the plane. The pull tabs may include a textured gripping surface.

The catheter securement device may include a recess adjacent the slit for receiving a portion of the catheter hub. The anchoring member may be generally symmetrical about at least one axis, and the slit may be generally disposed along one said axis. The anchoring member may be made of a flexible, low surface energy material.

In a specific embodiment, a catheter securement device in accordance with the present invention includes a flexible base member having an adhesive side and an opposite non-adhesive side. A single piece elastomeric anchoring member is mounted on the non-adhesive side of the base member. The anchoring member integrally includes a mounted portion and a receiving portion. The mounted portion is adhered to the base member, and the receiving portion is free from the base member. The receiving portion includes a pair of opposing pull tabs, a slit disposed between the opposing pull tabs, and a third pull tab disposed between the slit and one of the opposing pull tabs. A pocket is formed between the receiving portion and the base member and is open at the slit. Pulling the opposing pull tabs widens the slit for receiving a catheter hub in the pocket, and the third pull tab is insertable into the slit for securing the catheter hub between the anchoring member the said base member.

The third pull tab may extend at an angle relative to the base member. The base member and the pair of opposing pull tabs may be generally coplanar, and the third pull tab may be disposed at an angle relative to the plane. The pull tabs may include a textured gripping surface.

The catheter securement device may include a recess adjacent the slit for receiving a portion of the catheter hub. The anchoring member may be generally symmetrical about at least one axis, and the slit may be generally disposed along one said axis. The anchoring member may be made of a flexible, low surface energy material.

In another specific embodiment, a catheter securement device in accordance with the present invention includes a flexible base member having an adhesive side and an opposite non-adhesive side. A single piece elastomeric anchoring member is mounted on the non-adhesive side of the base member. The anchoring member integrally includes pairs of spacedly disposed feet adhered to the base member, and a pair of generally adjacent first and second straps connecting the feet. The first and second straps are free from attachment to the base member and define a slit therebetween. The anchoring member further integrally includes a pair of opposing pull tabs extending from the straps, and a third strap extending from one of the first and second straps and terminating in a third pull tab. A pocket is formed between the first and second straps and the base member, and is open at the slit. Pulling the opposing pull tabs widens the slit for receiving a catheter hub in the pocket, and the third pull tab is insertable into the slit for securing the catheter hub between the anchoring member, the base member, and the third strap.

The third pull tab may extend at an angle relative to the base member. The base member and the pair of opposing pull tabs may be generally coplanar, and the third pull tab may be disposed at an angle relative to the plane. The pull tabs may include a textured gripping surface.

A recess may be disposed between the feet adjacent the slit for receiving a portion of the catheter hub. The anchoring member may be generally symmetrical about at least one axis, and the slit may be generally disposed along one said axis. The anchoring member may be made of a flexible, low surface energy material.

Optionally, a raised surface (e.g., a dome) may be disposed on the non-adhesive side of the base member. The raised surface may be generally centered on the base member and may coincide with the pocket.

These and other features and advantages of the invention will be more fully understood from the following detailed description of the invention taken together with the accompanying drawings.

DETAILED DESCRIPTION OF THE INVENTION

Referring now to the drawings in detail, numeral 10 generally indicates a catheter securement device in accordance with the present invention. A bottom side of the securement device 10 can be adhered to a patient's skin. The securement device 10 then anchors a catheter by urgedly engaging catheter hub wings of a catheter inserted into a patient. Once the catheter is secured by the securement device 10, stresses and forces applied in any direction on luers and fittings connected to the catheter will not cause the catheter to move and thereby irritate the insertion site. The catheter wings are also easily removable from the securement device 10, allowing for replacement of the securement device without disturbing the catheter inserted in the insertion site.

Figure 1:
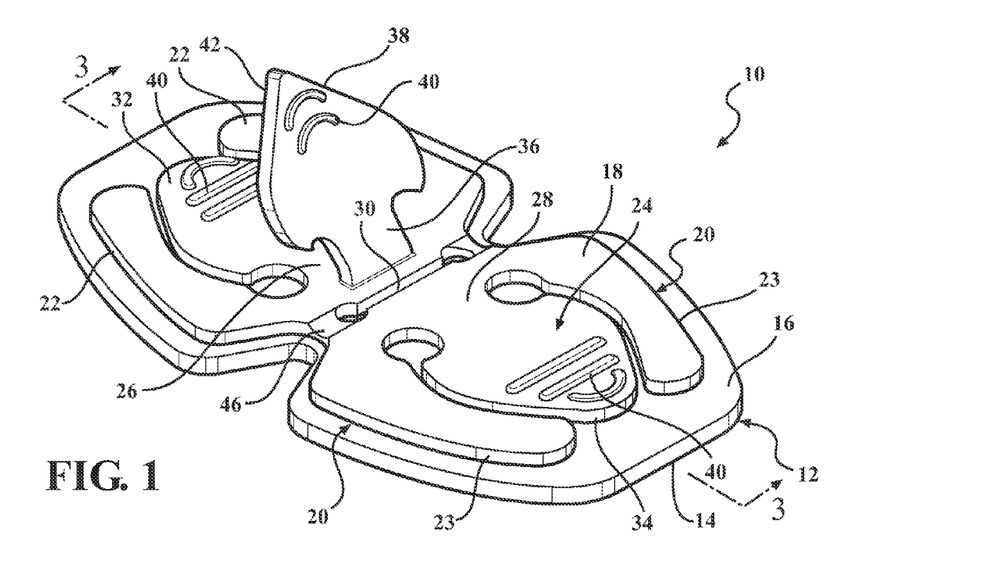
FIG. 1 is a perspective view of a catheter securement device in accordance with the present invention.
Figure 2:
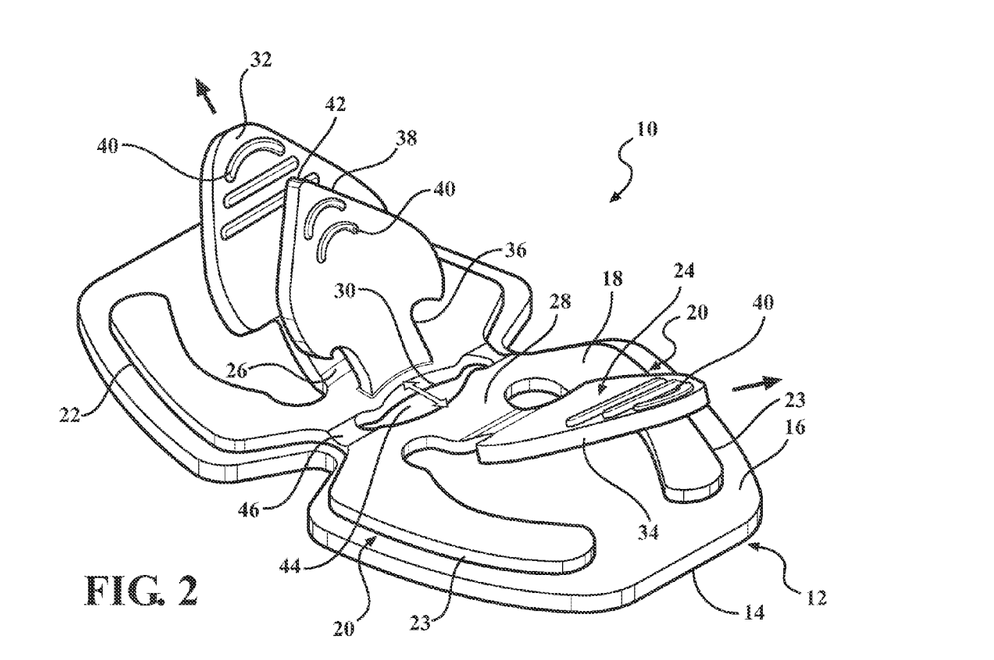
FIG. 2 is a perspective view of the catheter securement device of FIG. 1 illustrating opening of an anchoring member slit by a pulling force on an anchoring member tab.
Figure 3:
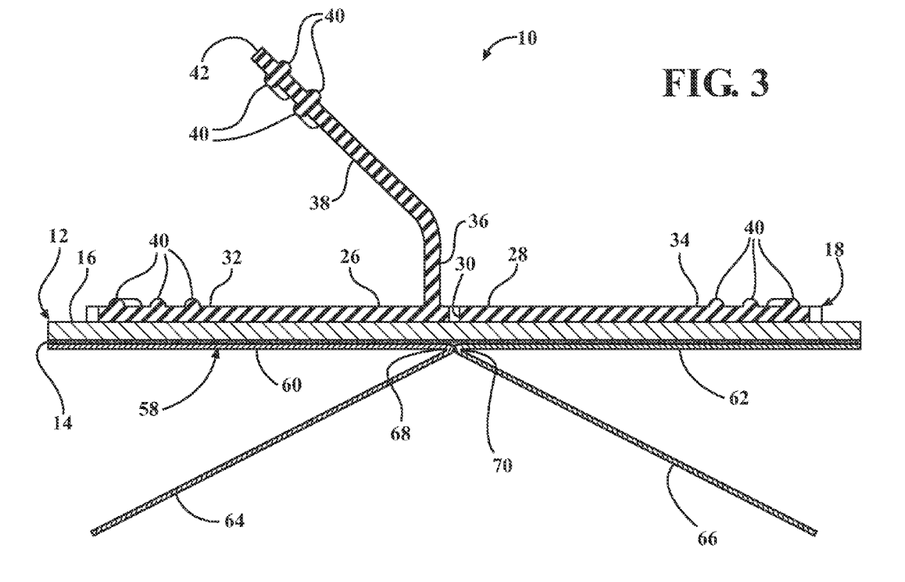
FIG. 3 is a cross-sectional view of the catheter securement device taken along the line 3-3 in FIG. 1.

Turning first to FIGS. 1 through 3, a catheter securement device 10 in accordance with the present invention includes a flexible base member 12 having an adhesive side 14 for adherence to a surface such as a patient's skin, and an opposite non-adhesive side 16. The surface of the adhesive side 14 includes an adhesive such as a medical grade adhesive or similar thereon. The base member 12 may be a generally flat, planar member, may be pad-like, and may be made of a foam, fabric, a laminate of foam/fabric/film, or similar material.

A single piece elastomeric anchoring member 18 is mounted on the non-adhesive side of the base member 12. The anchoring member 18 may be made of any suitable flexible, stretchable elastomeric material such as silicone, polyurethane, high friction rubber, or similar. The material of the anchoring member 18 is preferably low in surface energy (e.g., a silicone material) to prevent a medical dressing placed over the device 10 (in use on a patient) from sticking to the device upon removal. The anchoring member 18 integrally includes a mounted portion 20 including two pairs of spacedly disposed feet 22, 23 adhered to the base member 12. One pair of the feet 22 may generally face an opposite direction than the other pair of the feet 23, and each of these pairs of feet 22, 23 may be generally disposed on opposite halves of the base member 18.

The anchoring member also integrally includes a receiving portion 24 that is free from the base member 12. The receiving portion 24 includes a pair of generally adjacent first and second straps 26, 28. Each strap 26, 28 connects a different one of the pairs of feet 22, 23, i.e. strap 26 connects one of the pairs of feet 22 and strap 28 connects the other pair of feet 23. The straps 26, 28 are free from attachment to the base member 12 (are not adhered to the base member) and define a slit 30 therebetween. The anchoring member 18 may be generally symmetrical about a longitudinal axis and/or a transverse axis (i.e., x and y axes) of the securement device 10, and the slit 30 may be disposed along the transverse axis. Due to the symmetry of the anchoring member 18, the device 10 is designed for both right and left-handed use.

The receiving portion 24 further integrally includes a pair of opposing pull tabs 32, 34. Pull tab 32 extends in one direction from strap 26 and pull tab 34 extends from strap 28 in a generally opposite direction such that the slit 30 is generally disposed between the pull tabs 32, 34. In a resting, non-use disposition of the securement device 10, the slit 30 is essentially closed (i.e., the straps 26, 28 may contact each other at the slit 30), while pulling the pull tabs 32, 34 in opposite directions moves the straps away from each other and thereby opens the slit. Pull tab 32 is generally disposed between one of the pairs of feet 22 and pull tab 34 is generally disposed between the other pair of feet 23. The receiving portion 24 also integrally includes a third strap 36 extending from either the first strap 26 or second strap 28 at an angle relative to the base member 12. In the drawings, the third strap 36 extends from the first strap 26, but could instead extend from the second strap 28. The third strap 36 terminates in a third pull tab 38 and is generally disposed between the slit 30 and the pull tab 32. The angular bend of the third strap 36 may form an angle with the base member 12 that is in the range of 0 to 180 degrees, and may preferably be within the range of 20 to 30 degrees, although angles smaller than 20 degrees or larger than 30 degrees are within the scope of the invention. In the resting, non-use disposition of the securement device 10, the base member 12 and the opposing pull tabs 32, 34 are generally coplanar, if the plane is considered to have a thickness equal to the total thickness of the base member 12 and pull tabs 32, 34 (because the pull tabs 32, 34 are stacked on top of the base member 12). Alternatively, the base member 12 can be considered to lie in one plane, and the pull tabs 32, 34 can be considered to lie in an adjacent, parallel plane. In any event, the third pull tab 38 and the third strap 36 to which it is attached are disposed at an angle relative to this plane (or these parallel planes) such that the third pull tab lies in a separate plane that intersects this plane. In other words, the third pull tab 38 and third strap 36 are "out-of-plane" relative to the rest of the securement device 10.

The pull tabs 32, 34, 38 each may be generally spade-shaped and each may include a textured gripping surface 40 such as raised portions, bumps, dimples, scores, or similar that facilitates grasping of the pull tabs by a user's thumbs and fingers. The third pull tab 38 may have a pointed tip 42 that facilitates insertion of the third pull tab into the slit 30.

A pocket 44 is formed between the first and second straps 26, 28 of the receiving portion 24 and the non-adhesive side 16 of the base member 12. A catheter hub may be received in the pocket 44 through the slit 30 and held in the pocket by the three straps 26, 28, 36 as described in more detail below. The securement device 10 may also include a recess 46 such as a groove, channel, or similar that is adjacent the slit 30 and generally disposed between one foot 22 and one foot 23. A portion of a catheter hub may be received in the recess 46 when the catheter hub is held and secured by the securement device 10 (for example, see FIG. 5), facilitating the nestling of the catheter hub in the pocket 44.

Figure 4:
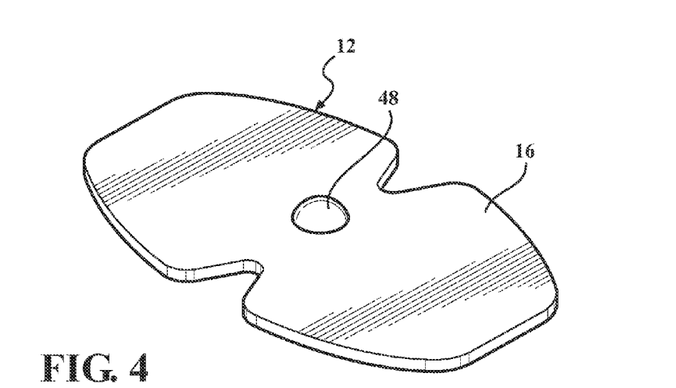
FIG. 4 is a partial view of a catheter securement device in accordance with the present invention illustrating a specific embodiment of a base member of the device.

As shown separately in FIG. 4, the non-adhesive side 16 of the base member 12 of the securement device may optionally include a raised surface 48 dome, hemisphere, or similar. The raised surface may be generally centered on the base member 12 such that its position generally coincides with the location of the pocket. The dome may have a diameter of approximately 0.25 inches, although it is not limited to this particular size. The raised surface 48 significantly reduces rising of cannula connected to the catheter hub when the catheter hub is secured in the securement device.

Also, the securement device 10 may include a release liner having a tackless side contacting the adhesive side 14 of the base member 12 to prevent the securement device from adhering to another object prior to its use (i.e., during storage). The release liner 58 generally extends at least to an edge of the base member 12. Optionally, the release liner 58 may include a first piece 60 and a second piece 62. The first and second pieces 60, 62 may be folded such that each of the first and second pieces have tabs 64, 66 formed by the folds 68, 70. One of the pieces can be released from the dressing without tampering with the other piece, which facilitates mounting of the securement device on a surface such as a patient's skin. The side of the securement device with the release liner removed can be placed on the patient's skin while the other side of the securement device with the release liner in place can be held without sticking to the user's thumb and fingers.

Turning to FIGS. 1 and 5 through 7, for purposes of example the securement device 10 is shown securing a PICC 50 (Peripherally Inserted Central Catheter). First, a health care provider, herein a nurse for illustrative purposes, inserts the catheter 50 through a patient's skin at an insertion site 52. After insertion of the catheter 50, the nurse removes one piece of the release liner that may be present on the adhesive side 14 of the securement device 10 by pulling on the release liner tab. This exposes part of the adhesive side 14 of the base member 12, which the nurse mounts on the patient's skin such that the slit 30 is positioned below/underneath the catheter hub 54 and the opposing pull tabs 32, 34 are generally positioned below/underneath the catheter hub wings 56. The nurse then removes the other piece of the release liner by pulling on the release liner tab to expose the rest of the adhesive side 14 of the base member 12. The base member 12 is then fully adhered to the patient's skin.

Figure 5:
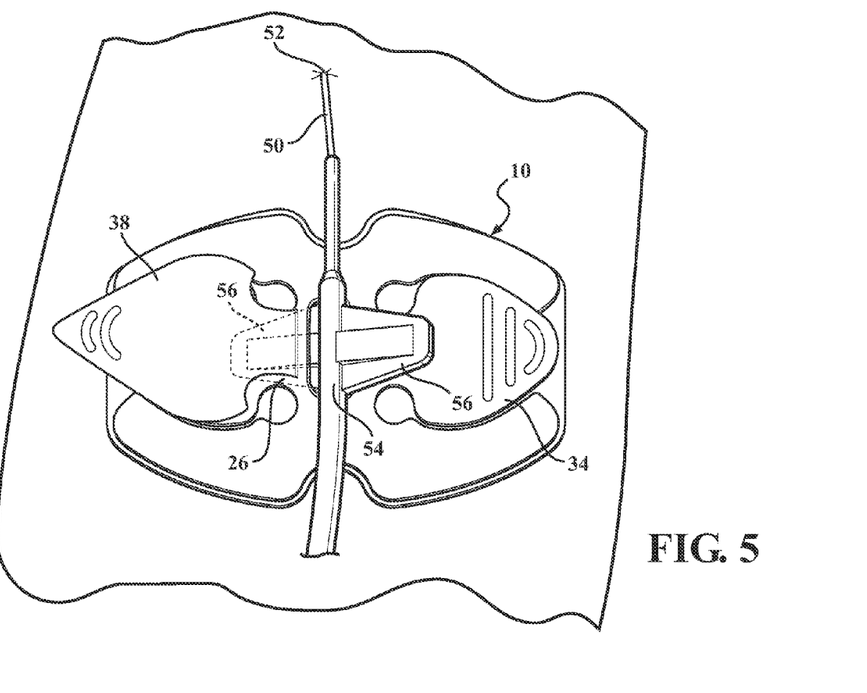
FIG. 5 is an environmental view of the catheter securement device of FIG. 1 adhered to a patient's skin, and illustrating a method of anchoring a catheter hub in which one catheter wing extending from the hub has been secured.
Figure 6:
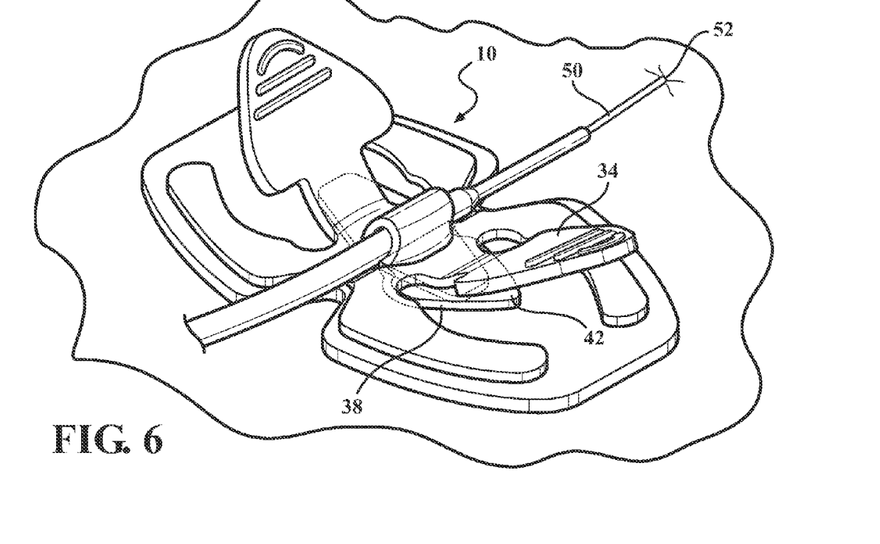
FIG. 6 is an environmental view illustrating the method of anchoring the catheter hub in which a third pull tab is inserted through a slit to secure the catheter hub.
Figure 7:
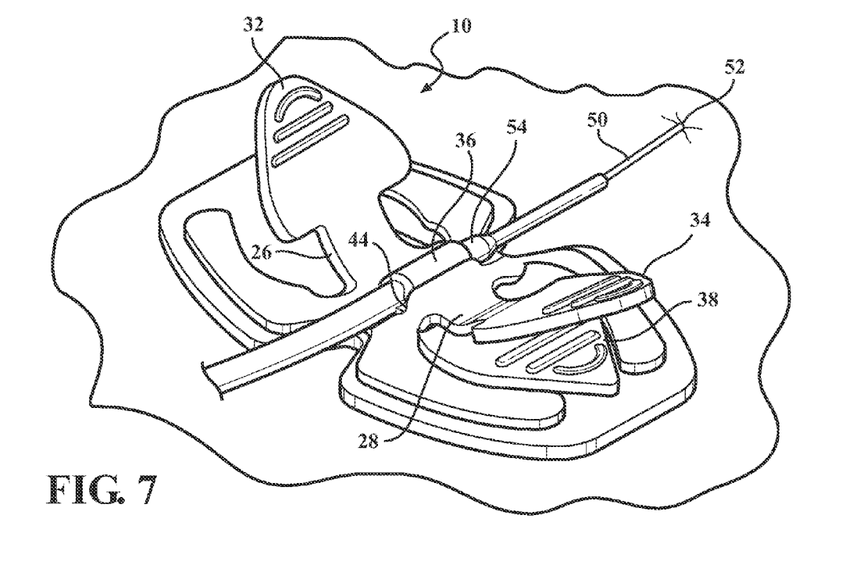
FIG. 7 is an environmental view illustrating the catheter hub completely secured in the securement device.

At this point, the nurse may hold the catheter 50 in place with one finger and use his/her other hand to pull on pull tab 32 which is on the same side as the third strap 36 and third pull tab 38. Pulling/stretching of pull tab 32 stretches the first strap 26 and opens the slit 30 as shown in FIG. 2. The catheter wing 56 on the same side as the stretched pull tab 32 is inserted through the slit 30 into the pocket 44 so that it is disposed underneath the pull tab 32 and first strap 26. The nurse then releases the pull tab 32, which secures the catheter wing 56 as shown in FIG. 5. After securing one catheter wing 56, the nurse pulls/stretches pull tab 34 to open the slit 30 and inserts the other catheter wing 56 through the slit 30 into the pocket 44 so that it is disposed underneath the pull tab 34 and second strap 28. As shown in FIG. 6, while still holding and stretching the pull tab 34 to keep the slit 30 open, the nurse grips the third pull tab 38 with his/her other hand and inserts the third pull tab 38, starting with the pointed tip 42, into and through the slit 30 such that the third strap 36 is disposed over the top of the catheter hub 54. The nurse then releases the pull tab 34 to secure the catheter wing 56 under the second strap 28. In this disposition, the second strap 28 also secures the third strap 36. The straps 26, 28, 36 engage the catheter hub 54 and wings 56, and the elasticity of the straps provides a constant force against the catheter hub and wings to securely hold the catheter hub and wings in the pocket 44, as shown in FIG. 7. Due to the material of construction of the anchoring member 18, there is also a significant amount of friction between the straps 26, 28, 36 and the catheter hub and wings 56, 58, which also aids in preventing movement of the catheter 50 and hub 56.

Figure 8:
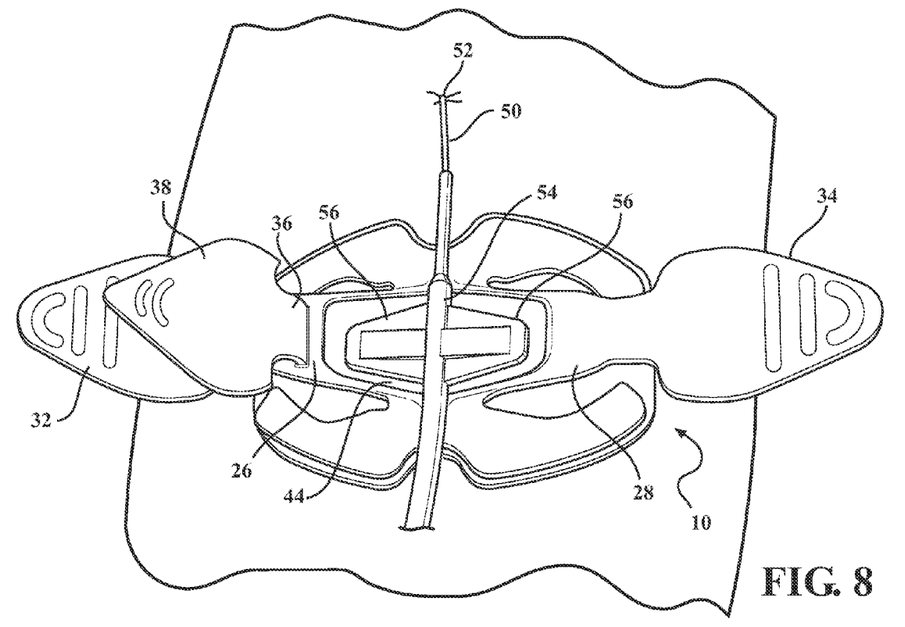
FIG. 8 is an environmental view illustrating a method of releasing the catheter hub from the securement device.

To remove the catheter hub 54 from the securement device 10, the nurse simply grips both of the opposing pull tabs 32, 34 and pulls them outwardly away from each other as shown in FIG. 8. This completely opens the slit 30 and also releases the third strap 36. The catheter hub 54 is then moved out of the pocket 44 and away from the securement device 10. Since no adhesive ever touches the catheter hub 54 or wings 56, the catheter hub cannot become stuck in the securement device 10, and the catheter 50 inserted in the patient's skin is not disturbed (e.g., not pulled or tugged on) when the catheter hub is released from the securement device 10.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A catheter securement device comprising:
  a flexible base member having an adhesive side and an opposite non-adhesive side;
  a single piece elastomeric anchoring member mounted on a top surface of the non-adhesive side of the base member;
  said anchoring member integrally including a mounted portion adhered to said base member and a receiving portion free of said base member; wherein the receiving portion includes first and second pull tabs, separated from one another, wherein the first and second pull tabs are selectively moveable independently from the mounted portion and independently from one another, a slit defined by adjacent edges of the receiving portion disposed through the anchoring member between said first and second pull tabs, inboard of an outer edge of the anchoring member, wherein the slit is essentially closed when the catheter securement device is in a non-use disposition, and a third pull tab extending from a top surface of the receiving portion and disposed between said slit and one of said first and second pull tabs, wherein the third pull tab is moveable independently from the first and second pull tabs;

wherein the slit is open when the first and second pull tabs are pulled away from one another such that the adjacent edges of the receiving portion are moved away from one another in a use position to define an opening for receiving a catheter hub in said slit, and said third pull tab being insertable into said slit for securing the catheter hub between said anchoring member and said base member.

2. The catheter securement device of claim 1, wherein said third pull tab extends at an angle relative to said base member.

3. The catheter securement device of claim 2, wherein said angle is generally in the range of approximately 0 to 180 degrees.

4. The catheter securement device of claim 1, wherein said base member and said first and second pull tabs are generally coplanar, and said third pull tab being disposed at an angle relative to a plane.

5. The catheter securement device of claim 1, including a recess extending from each of said first and second ends defining said slit, said recess formed in an upper surface of said anchoring member for receiving a portion of said catheter hub.

6. The catheter securement device of claim 1, wherein said anchoring member is generally symmetrical about at least one axis, and said slit is generally disposed along said at least one axis.

7. The catheter securement device of claim 1, wherein said pull tabs include a textured gripping surface.

8. The catheter securement device of claim 1, wherein said anchoring member is made of a flexible, low surface energy material.

9. The catheter securement device of claim 1, wherein a pocket is formed between said receiving portion and said base member, wherein the pocket is in communication with said slit; and wherein when said first and second pull tabs open said slit, the catheter hub is received in said pocket, through the slit, such that the catheter hub is positioned underneath the first and second pull tabs.

10. The catheter securement device of claim 9, wherein said third pull tab extends at an angle relative to said base member.

11. The catheter securement device of claim 9, wherein said base member and said first and second pull tabs are generally coplanar, and said third pull tab being disposed at an angle relative to a plane.

12. The catheter securement device of claim 9, including a recess formed in an upper surface of said receiving portion of said anchoring member, adjacent said slit for receiving a portion of said catheter hub.

13. The catheter securement device of claim 9, wherein said anchoring member is generally symmetrical about at least one axis, and said slit is generally disposed along said at least one axis.

14. The catheter securement device of claim 9, wherein said pull tabs include a textured gripping surface.

15. The catheter securement device of claim 9, wherein said anchoring member is made of a flexible, low surface energy material.

16. The catheter securement device of claim 1, wherein the anchoring member integrally includes a first and a second pair of spacedly disposed feet adhered to said base member, and a pair of substantially adjacent first and second straps, a first strap from the pair of straps connecting said first pair of feet, and a second strap from the pair of straps connecting said second pair of feet, said first pair of feet and said second strap connecting said second pair of feet, second straps not being adhered to said base member and defining the slit therebetween; wherein the first pull tab extends from said first strap and wherein the second pull tab extends from the second strap, wherein the anchoring member further integrally includes a third strap extending from one of said first and second straps and terminating in the third pull tab.

17. The catheter securement device of claim 16, wherein said third pull tab extends at an angle relative to said base member.

18. The catheter securement device of claim 16, wherein said base member and said first and second pull tabs are generally coplanar, and said third pull tab being disposed at an angle relative to a plane.

19. The catheter securement device of claim 16, including a recess disposed between said first and second pair of spacedly disposed feet and adjacent said slit for receiving a portion of said catheter hub.

20. The catheter securement device of claim 16, wherein said anchoring member is generally symmetrical about at least one axis, and said slit is generally disposed along said at least one axis.

21. The catheter securement device of claim 16, wherein said pull tabs include a textured gripping surface.

22. The catheter securement device of claim 16, wherein said anchoring member is made of a flexible, low surface energy material.

23. The catheter securement device of claim 16, including a raised surface on the non-adhesive side of said base member, said raised surface being generally centered on said base member and coinciding with a pocket formed between said receiving portion and said base member and open at said slit for receiving the catheter hub in said pocket when said opposing pull tabs open said slit.

\* \* \* \* \*

UNITED STATES PATENT AND TRADEMARK OFFICE
CERTIFICATE OF CORRECTION

| | |
|---|---|
| PATENT NO. | : 9,486,613 B2 |
| APPLICATION NO. | : 12/914220 |
| DATED | : November 8, 2016 |
| INVENTOR(S) | : Aaron M. Dickert et al. |

It is certified that error appears in the above-identified patent and that said Letters Patent is hereby corrected as shown below:

Column 8, Line 21, Claim 16:
After "said second pair of feet,"
Insert --said first and--

Signed and Sealed this
Eleventh Day of April, 2017

Michelle K. Lee
*Director of the United States Patent and Trademark Office*